US010874323B2

(12) United States Patent
Marcarian et al.

(10) Patent No.: US 10,874,323 B2
(45) Date of Patent: *Dec. 29, 2020

(54) SYSTEMS AND METHODS FOR PROVIDING BIOMETRIC RELATED TO PERFORMANCE OF A PHYSICAL MOVEMENT

(71) Applicant: PRECISION BIOMETRICS, INC., Seattle, WA (US)

(72) Inventors: David Marcarian, Seattle, WA (US); Michael Lawrence Peters, Seattle, WA (US)

(73) Assignee: Precision Biometrics, Inc., Seattle, WA (US)

( * ) Notice: Subject to any disclaimer, the term of this patent is extended or adjusted under 35 U.S.C. 154(b) by 198 days.

This patent is subject to a terminal disclaimer.

(21) Appl. No.: 15/948,208

(22) Filed: Apr. 9, 2018

(65) Prior Publication Data
US 2019/0082995 A1    Mar. 21, 2019

Related U.S. Application Data (63) Continuation of application No. 13/156,222, filed on Jun. 8, 2011, now Pat. No. 9,936,891.

(51) Int. Cl.
*A61B 5/0488*  (2006.01)
*A61B 5/00*  (2006.01)
(Continued)

(52) U.S. Cl.
CPC ............ *A61B 5/0488* (2013.01); *A61B 5/486* (2013.01); *G06Q 10/103* (2013.01);
(Continued)

(58) Field of Classification Search
CPC combination set(s) only.
See application file for complete search history.

(56) References Cited

U.S. PATENT DOCUMENTS 5,085,226 A    2/1992  DeLuca et al.
5,462,065 A *  10/1995  Cusimano ............ A61B 5/0488
                                                              600/595

(Continued)

FOREIGN PATENT DOCUMENTS

WO    2001/072223 A2    10/2001
WO    2009028221 A1     3/2009

OTHER PUBLICATIONS

European Search Report for EP Application No. 12796783.4 dated Nov. 5, 2014, 9 pages.

(Continued)

*Primary Examiner* — Sean P Dougherty
(74) *Attorney, Agent, or Firm* — John W. Branch; Branch Partners PLLC (57) ABSTRACT

A biometric feedback system for providing biometric feedback to a subject while the subject performs a controlled physical movement includes an applied-force-recording interface and at least one controller electrically coupled to the applied-force-recording interface. The at least one controller receives applied force from the subject during the controlled physical movement and the applied-force-recording interface records data related to the applied force. The biometric feedback system also includes a dynamic surface electromyograph ("sEMG") device that detects muscle tension along at least one muscle group of the subject while the subject performs the controlled physical movement and records data related to the muscle tension. A hub receives and processes data from the applied-force-recording interface and the dynamic sEMG device. A visual display displays the processed data from the hub.

20 Claims, 7 Drawing Sheets

(51) Int. Cl.
*G09B 15/00* (2006.01)
*G09B 15/06* (2006.01)
*G06Q 10/10* (2012.01)
*G09B 19/00* (2006.01)
*A61B 5/11* (2006.01)

(52) U.S. Cl.
CPC ........... *G09B 15/002* (2013.01); *G09B 15/06* (2013.01); *G09B 19/003* (2013.01); *A61B 5/0002* (2013.01); *A61B 5/1124* (2013.01); *A61B 5/4519* (2013.01); *A61B 2505/09* (2013.01)

(56) References Cited

U.S. PATENT DOCUMENTS

| | | | |
|---|---|---|---|
| 5,505,208 A * | 4/1996 | Toomim | A61B 5/0488 600/546 |
| 5,513,651 A * | 5/1996 | Cusimano | A61B 5/0488 600/595 |
| 5,662,118 A * | 9/1997 | Skubick | A61B 5/04004 600/546 |
| 5,679,004 A | 10/1997 | McGowan et al. | |
| 5,964,719 A | 10/1999 | Costello et al. | |
| 6,007,459 A | 12/1999 | Burgess | |
| 6,063,046 A * | 5/2000 | Allum | A61B 5/1036 600/595 |
| 6,613,000 B1 | 9/2003 | Reinkensmeyer et al. | |
| 7,593,769 B1 * | 9/2009 | Ettare | A61B 5/0488 600/547 |
| 7,708,700 B2 | 5/2010 | Ghajar | |
| 2001/0049482 A1 | 12/2001 | Pozos et al. | |
| 2002/0198473 A1 | 12/2002 | Kumar et al. | |
| 2004/0220490 A1 | 11/2004 | Appel et al. | |
| 2004/0237757 A1 | 12/2004 | Alling | |
| 2005/0005761 A1 | 1/2005 | Knudsen | |
| 2005/0113710 A1 | 5/2005 | Stahmann et al. | |
| 2005/0187071 A1 * | 8/2005 | Yamashita | D04B 1/102 482/1 |
| 2006/0027079 A1 | 2/2006 | Uehara | |
| 2006/0058699 A1 | 3/2006 | Vitiello et al. | |
| 2006/0123976 A1 | 6/2006 | Both et al. | |
| 2007/0179534 A1 | 8/2007 | Firlik et al. | |
| 2008/0153672 A1 | 6/2008 | Barre et al. | |
| 2009/0023122 A1 | 1/2009 | Lieberman et al. | |
| 2009/0048081 A1 | 2/2009 | Kamins | |
| 2009/0054804 A1 * | 2/2009 | Gharib | A61B 5/7405 600/554 |
| 2009/0062696 A1 | 3/2009 | Nathan et al. | |
| 2009/0098519 A1 | 4/2009 | Byerly | |
| 2009/0188369 A1 | 7/2009 | Chen et al. | |
| 2009/0233768 A1 | 9/2009 | Merzenich et al. | |
| 2009/0270768 A1 | 10/2009 | Lee | |
| 2009/0299210 A1 | 12/2009 | Marcarian | |
| 2010/0145219 A1 * | 6/2010 | Grey | A61B 5/0488 600/546 |
| 2011/0004126 A1 | 1/2011 | Einav et al. | |
| 2011/0052005 A1 | 3/2011 | Selner | |
| 2011/0137196 A1 | 6/2011 | Kakei et al. | |
| 2011/0213267 A1 | 9/2011 | Kakei et al. | |
| 2011/0259176 A1 | 10/2011 | Pillhofer et al. | |
| 2011/0283866 A1 | 11/2011 | Hogan | |

OTHER PUBLICATIONS

"Using EMG data to constrain optimization procedure improves finger tendon tension estimations during static fingertip force production" Vigouroux Journal of Biomechanics 40 (2007) 2846-2856.

"Assessment of dynamic finger forcees in pianists: Effects of training and expertise" Parlitz et al. Journal of Biomechanics 31 (1998) 1063-1067.

"Large index-fingertip forces are produced by subject-independent patterns of muscle excitation" Valero-Cuevas Journal of Biomechanics 31 (1998) 693-703.

"The Use of Multimodal Feedback in Retraining of Complex Technical Skills of Piano Performance" Riley et al. Medical Problems of Performing Artists Jun. 2005, pp. 82-88.

Sensor-Based Feedback for Piano Pedagogy, Aristotelis Hadjokos 2011, 173 pages.

International Search Report and Written Opinion for International Application PCT/US2012/041140 dated Jan. 31, 2013, 12 pages.

Official Communication for U.S. Appl. No. 13/156,222 dated Dec. 28, 2017, 16 pages.

Official Communication for U.S. Appl. No. 13/156,222 dated Oct. 16, 2017, 3 pages.

Official Communication for U.S. Appl. No. 13/156,222 dated Jul. 10, 2017, 79 pages.

Official Communication for U.S. Appl. No. 13/156,222 dated Jan. 12, 2017, 60 pages.

Official Communication for U.S. Appl. No. 13/156,222 dated May 19, 2016, 3 pages.

Official Communication for U.S. Appl. No. 13/156,222 dated Feb. 18, 2016, 38 pages.

Official Communication for U.S. Appl. No. 13/156,222 dated Sep. 8, 2015, 34 pages.

Official Communication for U.S. Appl. No. 13/156,222 dated Jun. 11, 2015, 3 pages.

Official Communication for U.S. Appl. No. 13/156,222 dated Mar. 12, 2015, 38 pages.

Official Communication for U.S. Appl. No. 13/156,222 dated Aug. 12, 2014, 45 pages.

Official Communication for U.S. Appl. No. 13/156,222 dated Jul. 11, 2014, 8 pages.

Official Communication for EP Patent Application No. 12796783.4 dated Mar. 24, 2020, pp. 1-5.

* cited by examiner

SYSTEMS AND METHODS FOR PROVIDING BIOMETRIC RELATED TO PERFORMANCE OF A PHYSICAL MOVEMENT

CROSS-REFERENCE TO RELATED APPLICATION

This Utility Patent Application is a Continuation of U.S. patent application Ser. No. 13/156,222 filed on Jun. 8, 2011, now U.S. Pat. No. 9,936,891 issued on Apr. 10, 2018, the benefit of which is claimed under 35 U.S.C. § 120, and the contents of which is further incorporated in entirety by reference.

TECHNICAL FIELD

The present invention is directed to a biometric feedback system. The present invention is also directed to methods of using the biometric feedback system to provide feedback to a subject during, or after, performance of a physical movement to facilitate improvement of the physical movement.

BACKGROUND

Many individuals aspire to improve performance of physical movements (e.g., playing musical instruments, playing sports, engaging in recreational activities, performing tasks, performing chores, or the like). Such individuals may range in level of ability from people with severe physical or neurological disorders or conditions to elite professional athletes or musicians. Diagnosing deficiencies of physical movements can be difficult. It can also be difficult for a third person to determine how to provide meaningful feedback to an individual regarding his or her performance of the physical movement. Existing techniques for providing feedback to individuals regarding deficiencies of physical movements may not be adequate due to one or more of lack of accuracy or excessive financial costs.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to a biometric feedback system. The present invention is also directed to methods of using the biometric feedback system to provide feedback to a subject during, or after, performance of a physical movement to facilitate improvement of the physical movement.

The methods, systems, and devices described herein may be embodied in many different forms and should not be construed as limited to the embodiments set forth herein. Accordingly, the methods, systems, and devices described herein may take the form of an entirely hardware embodiment, an entirely software embodiment or an embodiment combining software and hardware aspects. The methods described herein can be performed using any type of computing device, such as a computer, that includes a processor or any combination of computing devices where each device performs at least part of the process.

Suitable computing devices typically include mass memory and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Methods of communication between devices or components of a system can include both wired and wireless (e.g., RF, optical, or infrared) communications methods and such methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

Many individuals, regardless of their physical abilities, endeavor to improve performance of one or more physical movements. In some instances, individuals afflicted with neurological or physical disorders or conditions may find difficulty in performing physical movements that may seem routine to others. In which case, such individuals may seek diagnoses, therapies, or treatments in order to improve performance of such difficult physical movements. In other instances, some individuals endeavor to improve performance of a sport, or a musical instrument, or other activities involving specialized physical movements. In yet other instances, some elite athletes, musicians, or the like may seek to fine tune their already-exceptional physical abilities in their particular crafts.

For individuals endeavoring to improve performance of one or more physical movements, it may be useful to receive feedback from a third party while performing the physical movement at issue. Providing such feedback, however, may be difficult. Assessing an individual's physical capabilities can be inherently subjective. Additionally, pinpointing deficiencies in performance of physical movements may not be easy to quantify or interpret.

Over the years, several types of devices ("biometric devices") have been developed that can measure and record one or more personal biological traits of an individual. As herein described, some of these devices can be used in concert to measure and record data from the individual which may be helpful in providing biometric feedback to the individual related to the performance of a controlled physical movement. One such type of biometric device is a dynamic surface electromyograph ("sEMG"). A dynamic sEMG device includes measuring electrodes which detect muscle tension in muscle groups of an individual and a dynamic sEMG module which records the detected muscle tension. As herein described, dynamic sEMG devices can be used for recording muscle tension in muscle groups used by an individual as the individual performs a controlled physical movement.

Another such type of biometric device is an applied-force-recording device. An applied-force-recording device includes a controller upon which force can be applied and an interface that enables information about the applied force to be recorded. One example of an applied-force-recording interface is a musical instrument digital interface ("MIDI"), which is an industry-standard protocol that can be used as an electronic interface for recording music. As herein described, applied-force-recording devices can be used for recording at least one of: 1) an amount of force; or 2) duration of a force that is applied to a controller by the individual as the individual performs the controlled physical movement.

Controllers can be any suitable musical instrument configured and arranged to receive an applied-force-recording interface (e.g., keyboards, percussion instruments, wind instruments, stringed instruments, bowed instruments, or the like). Controllers can also be other instruments configured and arranged to receive an applied-force-recording interface including, for example, sports-related instruments (e.g., racquets, clubs, mallets, bats, sticks, thrusting weapons, or the like). Controllers can further be other instruments that are related to the performance of a physical activity and that are also configured and arranged to receive an applied-force-recording interface (e.g., instruments with tactile interfaces, such as handles, grips, buttons, knobs, switches, or the like).

Despite advancements in sEMG and applied-force-recording technologies (e.g., MIDI technologies), a tool for accurately and cost-effectively assessing one or more physical capabilities of an individual remains elusive. As a result of the inability to accurately or cost-effectively assess one or more physical capabilities of an individual during performance of a physical movement, the individual may not be able to perform physical movements at a level commensurate with their abilities. Accordingly, lost opportunities may be realized at a personal level, as well as at a societal level.

As herein described, a biometric feedback system is configured and arranged to facilitate improvement of an individual's physical movements by providing biometric feedback to the individual based on the individual's performance of a biometric test. The biometric feedback includes: 1) force data; and 2) muscle tension data. In some cases, the biometric feedback may also include capturing the biometric test using one or more video-recording devices. The biometric feedback can be visually displayed. In some cases, the biometric feedback may also include audio data. The audio data, optionally, can be recorded either through the one or more video-recording devices used to record video, or from a separate device with audio-recording capabilities.

A biometric test may include an individual ("a subject") performing a physical movement that involves the subject applying force to a controller (e.g., performing at least a portion of a musical composition on a musical instrument, using a sports-related device to perform a corresponding sports-related movement, or the like) coupled to the applied-force-recording interface. The biometric test may also include the subject performing the controlled physical movement while the subject is coupled to an sEMG module. Biometric feedback may be provided from the biometric test. In some instances, the biometric feedback is provided directly to the subject performing the controlled physical movement. In at least some cases, the biometric feedback may be provided to one or more clinicians that can review, diagnose, assess, or analyze the feedback of the biometric test. The one or more clinicians may also provide instruction, advice, tutelage, coaching, therapy, exercise options, treatment options, or the like to the subject, based on the feedback of the biometric test. The one or more clinicians can either be present at the site of the biometric test, or the one or more clinicians can be at a location that is remote from the location where the biometric test is performed (e.g., another room, another building, another neighborhood, another city, another country, or the like).

In at least some embodiments, the biometric feedback is provided in real time. The feedback of the biometric test can be displayed on a visual display, for example, a computer monitor, or the like. In at least some embodiments, two or more types of data (e.g., force data, muscle tension data, video, or the like) can be displayed concurrently. In some cases, audio may be provided concurrently with the displayed data. In at least some embodiments, feedback can be reviewed by the subject or the one or more clinicians instantly, or at a later time. In at least some embodiments, the biometric feedback can be recorded for subsequent use by the subject, the one or more clinicians, or one or more other people. In at least some embodiments, data can be collected from the subject over time using the biometric feedback system. In some cases, data analysis can be performed on data from the biometric feedback.

Figure 1:
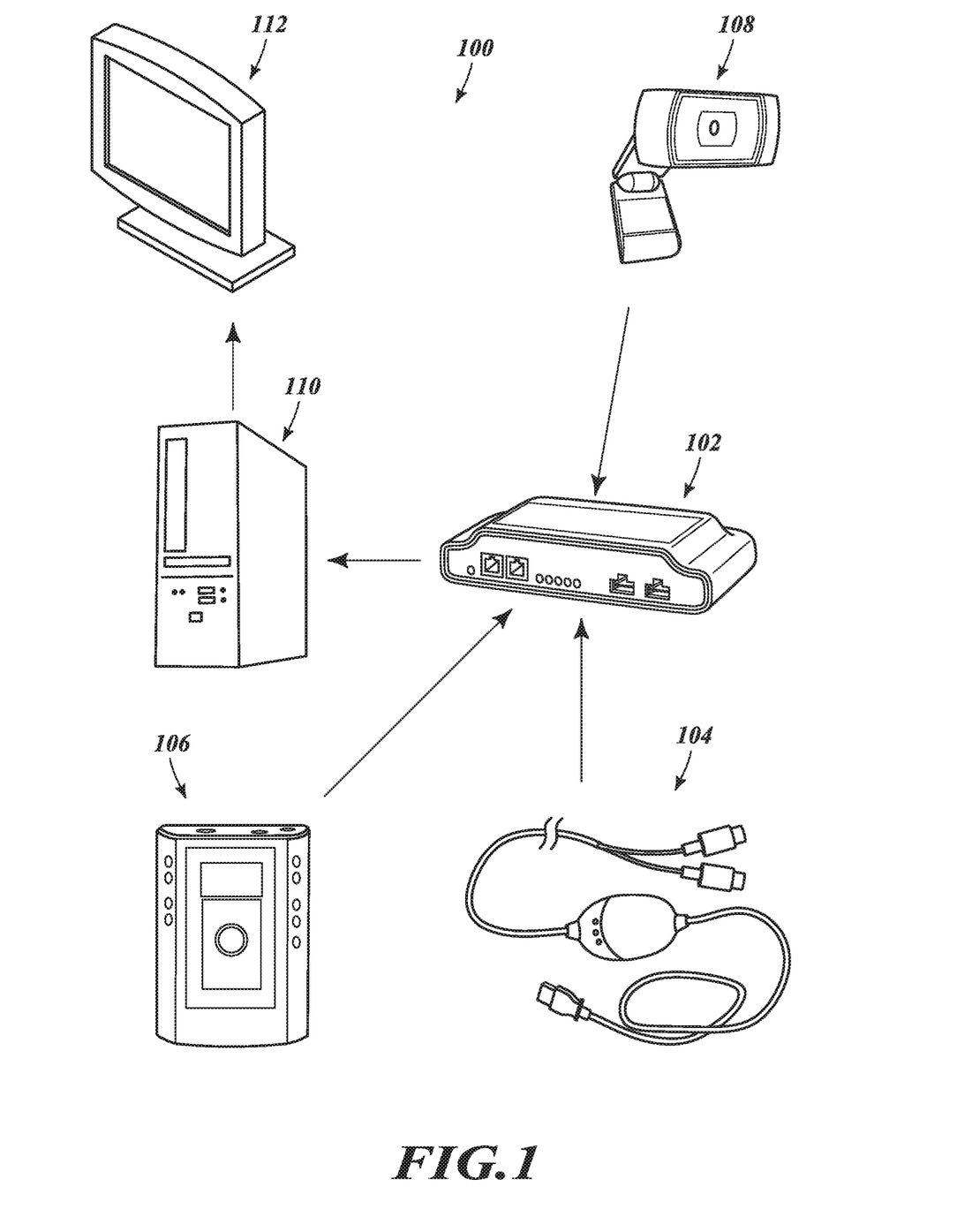
FIG. 1 is a schematic view of one embodiment of a biometric feedback system, according to the invention.

FIG. 1 is a schematic view of one embodiment of an exemplary biometric feedback system ("system") 100. The system 100 includes a hub 102, an applied-force-recording interface (e.g., a MIDI, or the like) 104 for use in recording force data from a controller (see e.g., 204 of FIG. 2 or 502 of FIG. 5) as the subject performs a controlled physical movement, and a dynamic sEMG control module ("sEMG module") 106 for use in recording muscle tension data from the subject as the subject performs the controlled physical movement.

In at least some embodiments, the applied-force-recording interface 104 and the dynamic sEMG module 106 are in electrical communication with the hub 102. In some embodiments, one or more of the applied-force-recording interface 104 and the dynamic sEMG module 106 are electrically coupled to the hub 102 by a wireless network, such as 3G or 4G. In other embodiments, one or more of the applied-force-recording interface 104 and the dynamic sEMG module 106 are electrically coupled to the hub 102 by one or more conductors, such as wires.

In at least some embodiments, the system 100 also includes one or more video-recording devices (e.g., webcams, video cameras, or the like) 108 for capturing still shots or video of the subject as the subject performs the controlled physical movement, one or more processors 110 to process data, and one or more displays 112 to display data. In at least some embodiments, the hub 102 is electrically coupled to the one or more processors 110. In at least some embodiments, the one or more processors 110 receive and process input data from the applied-force-recording interface 104 and the dynamic sEMG module 106 (via the hub 102) and display the results of the processed data on the one or more visual displays 112. In at least some embodiments, the hub 102 includes a USB connector. Thus, in at least some cases, the hub 102 can couple to the one or more processors 110 via a USB port of the one or more processors 110.

In at least some embodiments, the system 100 includes software or hardware for facilitating many different operations including, for example, linking the applied-force-recording interface 104 or the dynamic sEMG module 106 to the hub 102, performing the biometric test, displaying the results of the biometric test, saving and backing-up testing data, powering on or off the testing devices, or the like.

Figure 2:
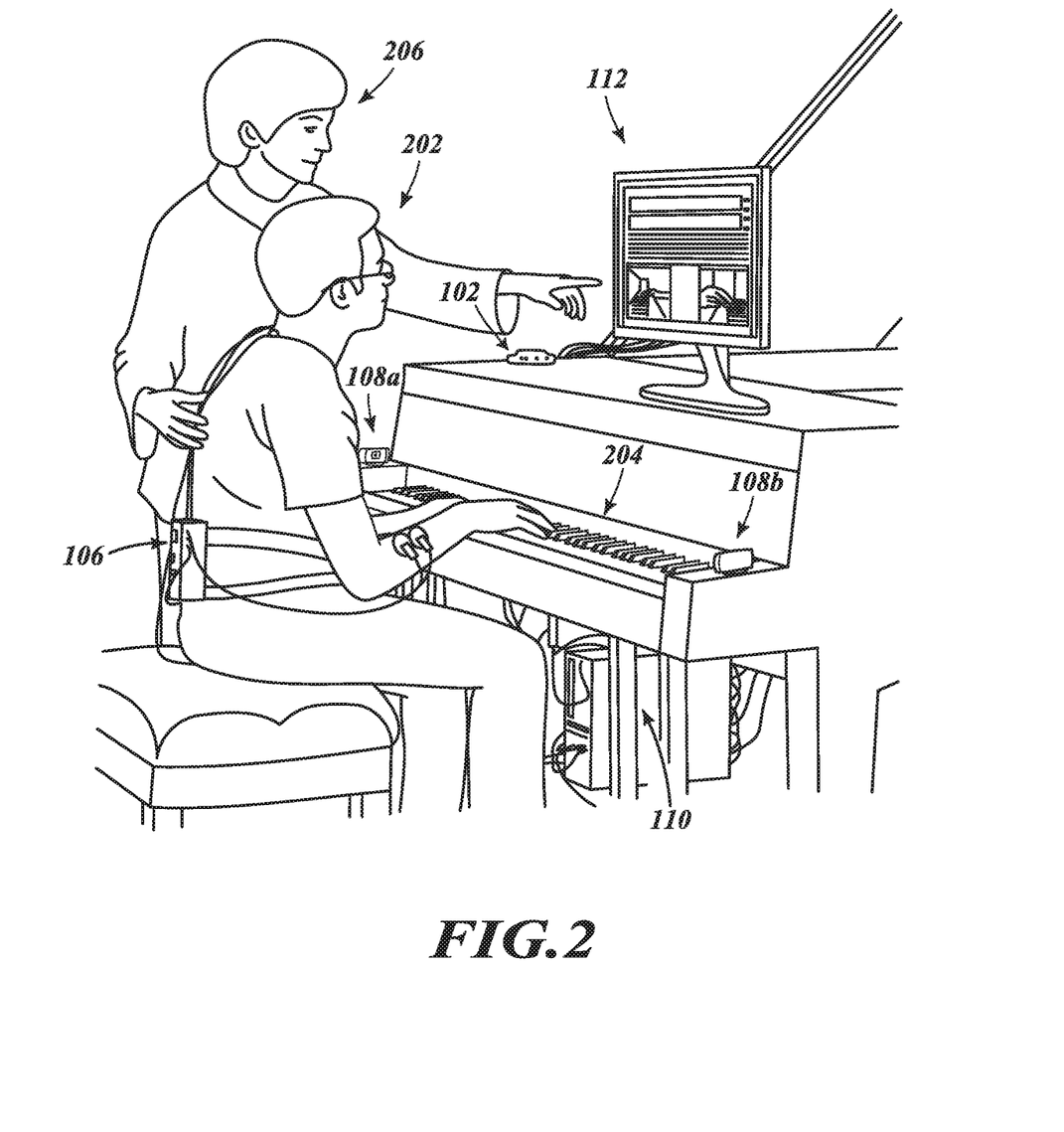
FIG. 2 is a schematic view of one embodiment of the biometric feedback system of FIG. 1 coupled to a subject as the subject plays a musical keyboard, according to the invention.

In at least some embodiments, the system 100 can be used to record data while the subject performs a physical movement that involves the subject applying force to one or more controllers (e.g., playing a musical instrument, using sports-related instrument, using some other instrument with a tactile interface, or the like). FIG. 2 is a schematic view of one embodiment of the system 100 coupled to a subject 202 as the subject 202 plays a musical keyboard 204. In the example shown in FIG. 2, the keyboard 204 is the controller upon which the subject 202 applies force, and the applied-force-recording interface 104 (not shown in FIG. 2) records force data from the keyboard 204 during the subject's performance.

The keyboard 204 is disposed on, for example, a MIDI-based piano, or the like. Accordingly, the keyboard 204 is coupled to the applied-force-recording interface 104. Additionally, the dynamic sEMG module 106 is coupled to the subject 202, and video-recording devices 108a and 108b are positioned at either end of the keyboard 204 and are oriented inward to capture video of the subject 202 as the subject 202 plays the keyboard 204. The results of the biometric test (e.g., two or more of force data, muscle tension data, and video from the subject's performance) can be concurrently displayed on the visual display 112.

In FIG. 2, a clinician 206 (e.g., a piano instructor, or the like) is shown observing the data displayed on the visual display 112 in real time. Thus, the clinician 206, the subject 202, or both are able to listen to the subject's performance and observe the simultaneous results from the performance. Accordingly, the system 100 enables the clinician 206 to provide real time feedback (e.g., instruction, or the like) to the subject 202 while the subject 202 is performing. Additionally, the system 100 enables the subject 202 to listen to the feedback from the clinician 206 and make corresponding physical adjustments to his performance as he continues to perform. The system 100 further enables the subject 202, or the clinician 206, or both to repeatedly listen to the performance, observe the results of the biometric test, and make physical adjustments to the subject's performance based on the results of the biometric test.

In the example shown in FIG. 2 of the subject 202 playing the keyboard 204, the clinician 206 is present at the location of the biofeedback test to listen to the music played by the subject. As mentioned above, one or more clinicians can be at a remote location. In which case, the one or more clinicians may need to be able to hear the music played, in order to further assess potential movement deficiencies. Accordingly, in at least some embodiments, the system 100 may additionally include one or more audio devices. In some cases, audio data can be captured using the one or more video devices 108.

Figure 3:
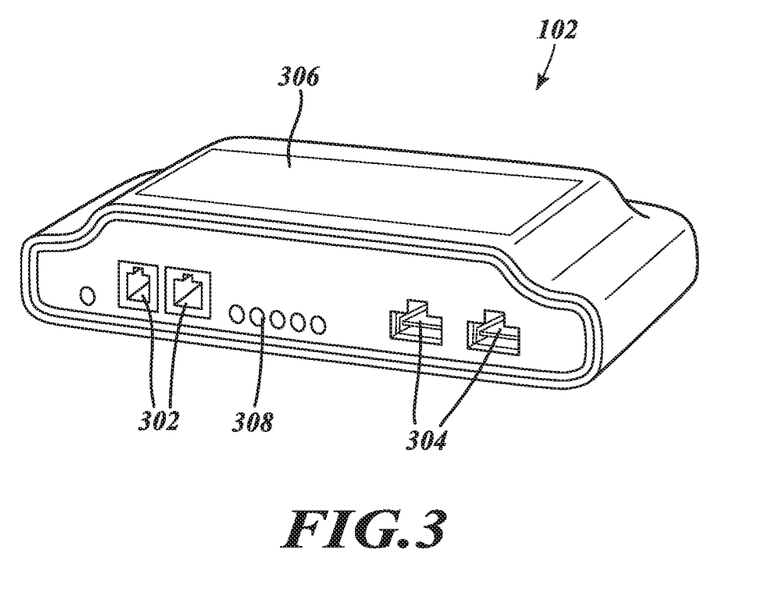
FIG. 3 is a schematic perspective view of one embodiment of a hub suitable for use with the biometric feedback system of FIG. 1, according to the invention.

FIG. 3 is a schematic perspective view of one embodiment of the hub 102. In at least some embodiments, the hub 102 includes one or more inputs 302 for coupling the applied-force-recording interface 104 or the dynamic sEMG module 106 to the hub 104. In at least some embodiments, the hub 102 also includes inputs 304 for one or more peripherals (e.g., a keyboard, a mouse, a monitor, a printer, a storage device, or the like). In at least some embodiments, the hub 102 includes one or more user interfaces 306 (e.g., displays, keypads, or the like). In at least some embodiments, the hub 102 includes one or more indicators 308, such as a power indicator, connectivity indicator, or the like. In at least some embodiments, multiple hubs 102 may be utilized, in parallel or in series. In at least some embodiments, the one or more hubs 102 receive and process input data from the applied-force-recording interface 104 or the dynamic sEMG module 106 and display the results on the visual display 112 coupled to (or disposed on) the hub 102. In at least some embodiments, the one or more hubs 102 include a keypad for inputting information.

Figure 4:
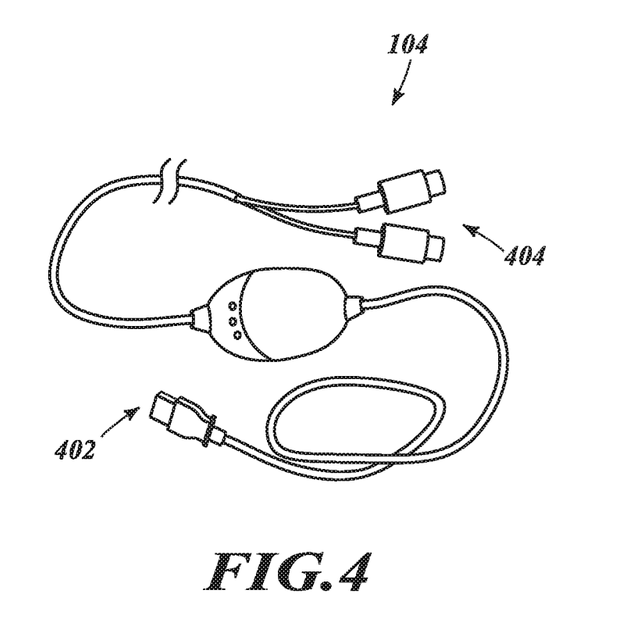
FIG. 4 is a schematic view of one embodiment of an applied-force-recording interface suitable for used with the biometric feedback system of FIG. 1, according to the invention.

FIG. 4 is a schematic view of one embodiment of the applied-force-recording interface 104. In FIG. 4, the applied-force-recording interface 104 is shown as a MIDI. The applied-force-recording interface 102 includes a first connector 402 for coupling to the hub 104 or the one or more processors 110, and a second connector 404 for coupling to a controller (e.g., the keyboard 204, or the like).

Figure 5:
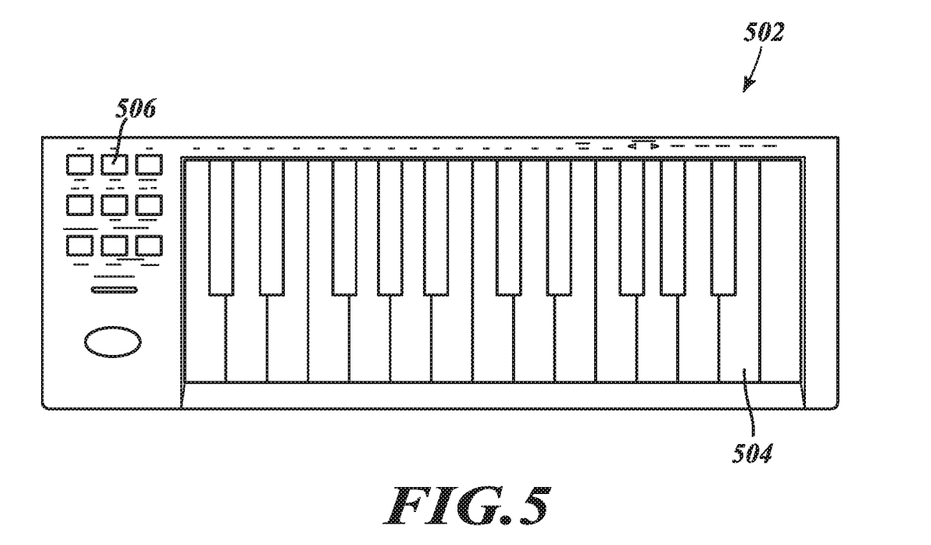
FIG. 5 is a schematic perspective view of one embodiment of a keyboard suitable for use with the applied-force-recording interface of FIG. 4, according to the invention.

As discussed above, many different types of controllers can be coupled to the applied-force-recording interface 104. FIG. 5 is a schematic perspective view of one embodiment of another keyboard 502 suitable for use with the system 100. The keyboard 502 includes keys, such as key 504, and user controls, such as user control 506, for adjusting one or more parameters of the keyboard 502.

Figure 6:
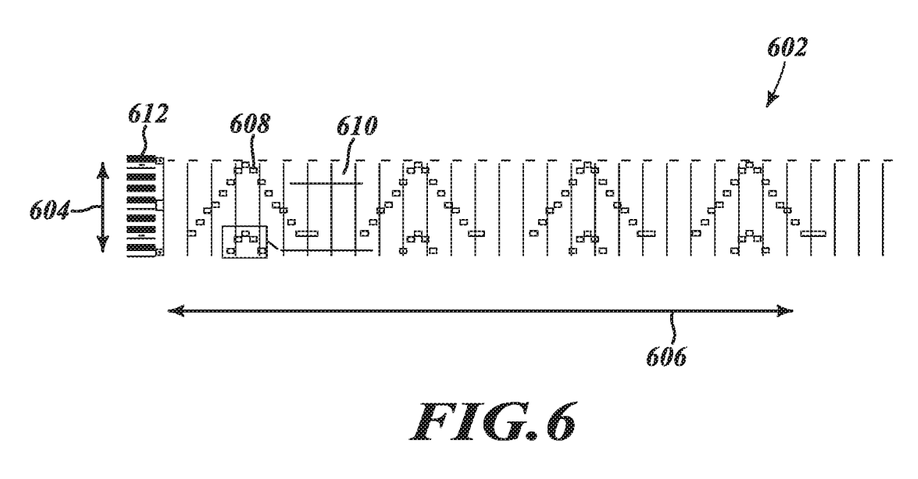
FIG. 6 is a schematic view of one embodiment of an exemplary display showing force data from a biometric test performed on a subject, the force data collected using an applied-force-recording interface and a musical keyboard, according to the invention.

When the subject 202 undergoes the biometric test (e.g., the subject 202 plays the keyboard 204, 502, or the like), the applied-force-recording interface 104 can record force data, and the one or more visual displays 112 can display the recorded force data. FIG. 6 is a schematic view of one embodiment of an exemplary display 602 of force data from a biometric test performed on the subject 202 while the subject 202 plays the keyboard 204, 502. Note that the exemplary display 602 of the force data can be displayed in many other different ways on the one or more visual displays 112.

In FIG. 6, the display 602 includes a graphical representation at least some keys 612 along a vertical axis 604 and time along a horizontal axis 606. Blocks, such as block 608, represent the striking of particular keys 612 at particular moments in time, for particular durations of time. Additional information 610 may also be included, such as which hand is being used by the subject 202, and the amount of force applied to one or more of the keys 612. It will be understood that the display 602 can include additional information, or less information.

Figure 7:
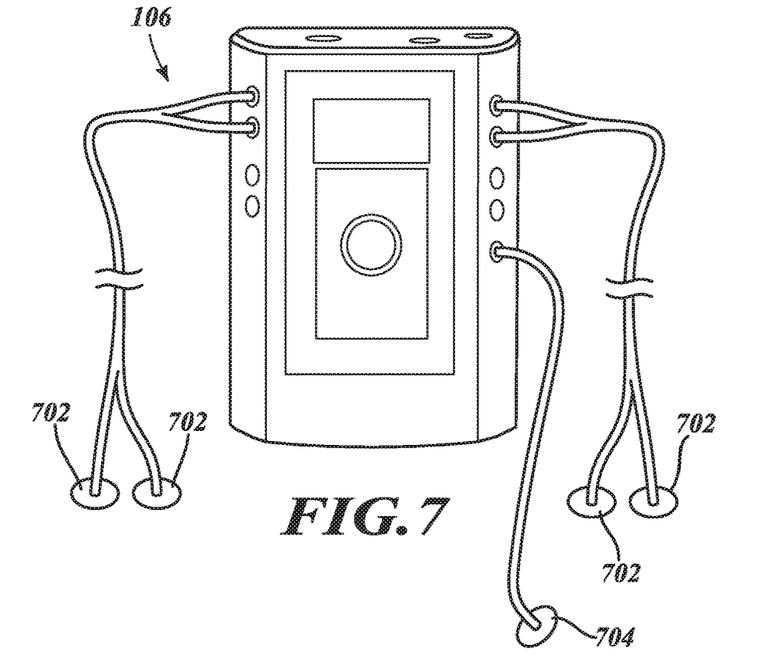
FIG. 7 is a schematic view of one embodiment of a dynamic surface electromyogram module and measuring electrodes suitable for use with the biometric feedback system of FIG. 1, according to the invention.

FIG. 7 is a schematic view of one embodiment of the sEMG module 106 of the system 100. In at least some embodiments, the sEMG module 106 is configured and arranged for measuring and recording muscle tension data from the subject 202 (e.g., measuring and recording action potentials along selected muscle groups as the subject 202 performs a controlled physical activity, such as playing the keyboard 204, 502). In at least some embodiments, measured and recorded muscle tension data is input to the hub 102 and processed by the hub 102 or by one or more processors 110.

In at least some embodiments, the sEMG module 106 is configured and arranged to receive measuring electrodes 702 that are coupleable to the subject 202. In at least some embodiments, the sEMG module 106 is configured and arranged to receive up to sixteen measuring electrodes 702 and a ground 704. The measuring electrodes 702 coupled to the sEMG module 106 may be formed from many different conductive materials suitable for placement against the skin of the subject 202 including, for example, gold, stainless steel, silver, silver chloride, and the like or combinations thereof. In at least some embodiments, multiple sEMG modules may be electrically coupled to one another or to the hub 102.

Figure 8:
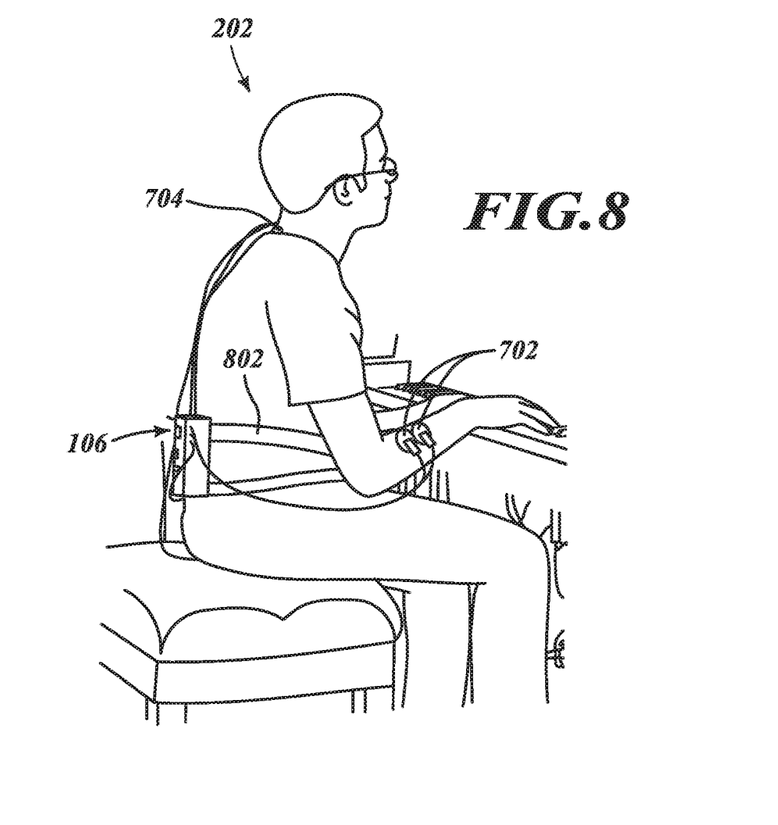
FIG. 8 is a schematic view of the dynamic surface electromyogram module of FIG. 7 coupled to a subject while the subject plays a musical keyboard, according to the invention.

FIG. 8 is a schematic view of the sEMG module 106 coupled to the subject 202, via the measuring electrodes 702, as the subject 202 plays the keyboard 204. In at least some embodiments, the measuring electrodes 702 are physically coupled to the subject 202 and electrically coupled to the sEMG module 106. In FIG. 8, the sEMG module 106 is coupled to a strap 802 (e.g., a belt, or the like) being worn by the subject 202.

The measuring electrodes 702 are positioned as determined by the muscle groups whose activity is to be measured during performance of the biometric test. For example, in FIG. 8, the measuring electrodes 702 are shown attached to outer surfaces of the subject's 202 forearms to measure the size and timing of action potentials as the subject 202 uses his forearm flexors and extensors (positioned within the subject's forearms below the measuring electrodes 702) to play the keyboard 204. In at least some embodiments, the ground 704 may also be used to couple the subject 202 to the sEMG module 106.

Figure 9:
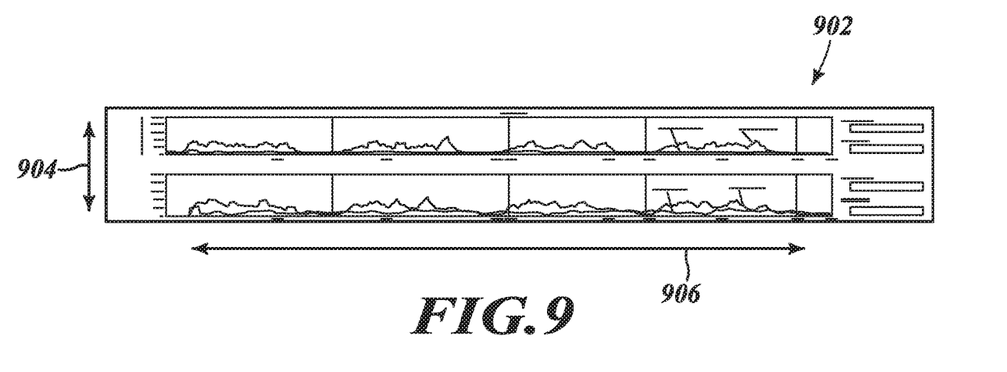
FIG. 9 is a schematic view of one embodiment of an exemplary display showing muscle tension data from a biometric test performed on a subject, the muscle tension data collected using a dynamic surface electromyogram module and measuring electrodes, according to the invention.

When the subject 202 undergoes the biofeedback test (e.g., the subject 202 plays the keyboard 204, 502, or the like), the sEMG module 106 can measure and record muscle tension data, and the one or more visual displays 112 can display the recorded muscle tension data. FIG. 9 is a schematic view of one embodiment of an exemplary display 902 of muscle tension data collected from a biometric test performed on the subject 202 while the subject 202 plays the keyboard 204, 502. Note that the exemplary display 902 of muscle tension data can be displayed in many other different ways on the one or more visual displays 112.

In FIG. 9, the display 902 shows voltages (e.g., action potentials of the forearm extensors, or the like) over time as the subject 202 plays the keyboard 204, 502. Voltage levels are shown along a vertical axis 904 and time is shown along a horizontal axis 906. In FIG. 9, the display 902 also shows voltages for the left and right trapezius muscles, in addition to showing the left and right forearm extensor muscles. It will be understood that the display 902 can include additional information (e.g., high, low, or average voltage levels for one or more particular muscle groups, or the like), or less information.

Figure 10:
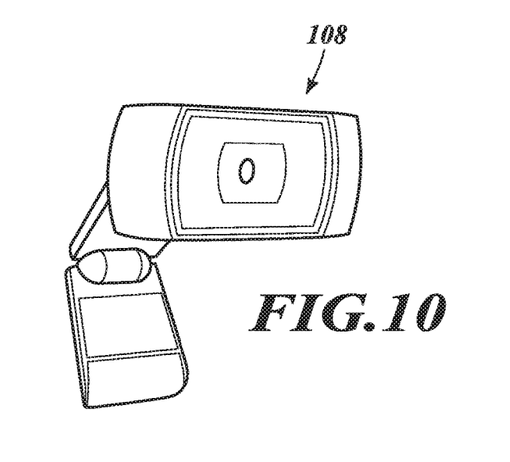
FIG. 10 is a schematic view of one embodiment of video-recording devices suitable for use with the biometric feedback system of FIG. 1, according to the invention.

In at least some embodiments, further insight into the subject's physical movements may be obtained by additionally including one or more video-recording devices, such as the video-recording device 108, to capture one or more static images or, preferably, a video image of the performance. FIG. 10 is a schematic view of one embodiment of the video-recording device 108. Any suitable video-recording device 108 may be used. In FIG. 10, the video-recording device 108 is shown as a webcam. It may be advantageous to use a webcam because webcams may be less expensive than other types of video-recording devices and may be easy to couple to other components of the system 100. Webcams may also be easier to couple with other hardware and software. Additionally, webcams can provide real-time data. In at least some embodiments, the video-recording device 108 includes a zoom function.

The positioning, orientation, and number of video-recording devices 108 can be varied, as needed, depending on the location and the type of physical movements being performed during the biometric test. In the exemplary performance shown in FIG. 2, the subject 202 is playing the keyboard 204. In that example, two video-recording devices 108 are positioned on opposing ends of the keyboard 204 and are oriented such that the two video-recording devices 108 face one another. Thus, with this positioning and orientation, the video-recording devices 108 can record hand movement from a side view, for example, to highlight hand posture and positioning, while the subject 202 plays the keyboard 204. It will be understood that other positioning and orientation of the video-recording devices 108 can be used in lieu of, or in addition to, the positioning and orientation of the video-recording devices 108 shown in FIG. 10.

Figure 11:
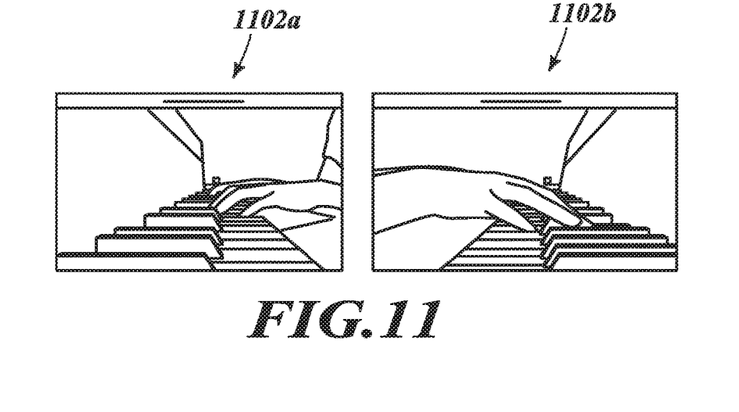
FIG. 11 is a schematic view of one embodiment of exemplary video frames captured from a biometric test performed on a subject, the video frames captured using video-recording devices, according to the invention.

FIG. 11 is a schematic view of one embodiment of exemplary video frames 1102a and 1102b captured from a biometric test performed on the subject 202 while the subject 202 plays the keyboard 204. The video frames 1102a and 1102b are captured using the video-recording devices 108a and 108b, respectively. In at least some embodiments, the captured images or videos may be made available for review by one or more clinicians, such as the clinician 206 in FIG. 2.

In at least some embodiments, one or more of the force data, the muscle tension data, and the videos (or static images) may be stored on the hub 102, one or more processors 112, or a storage device, and arranged such that the one or more clinicians may use a slider to play back the subject's motion (for example, a forward flexion) and determine precisely the amount of the force, the timing of the force, and the muscle tension of applicable muscle groups, along with video of the subject's body showing the precise manner of movement. Moreover, similar testing may subsequently be performed on the same subject. Thus, comparison of two or more data sets may be performed to provide data for tracking subject progress over time.

Figure 12:
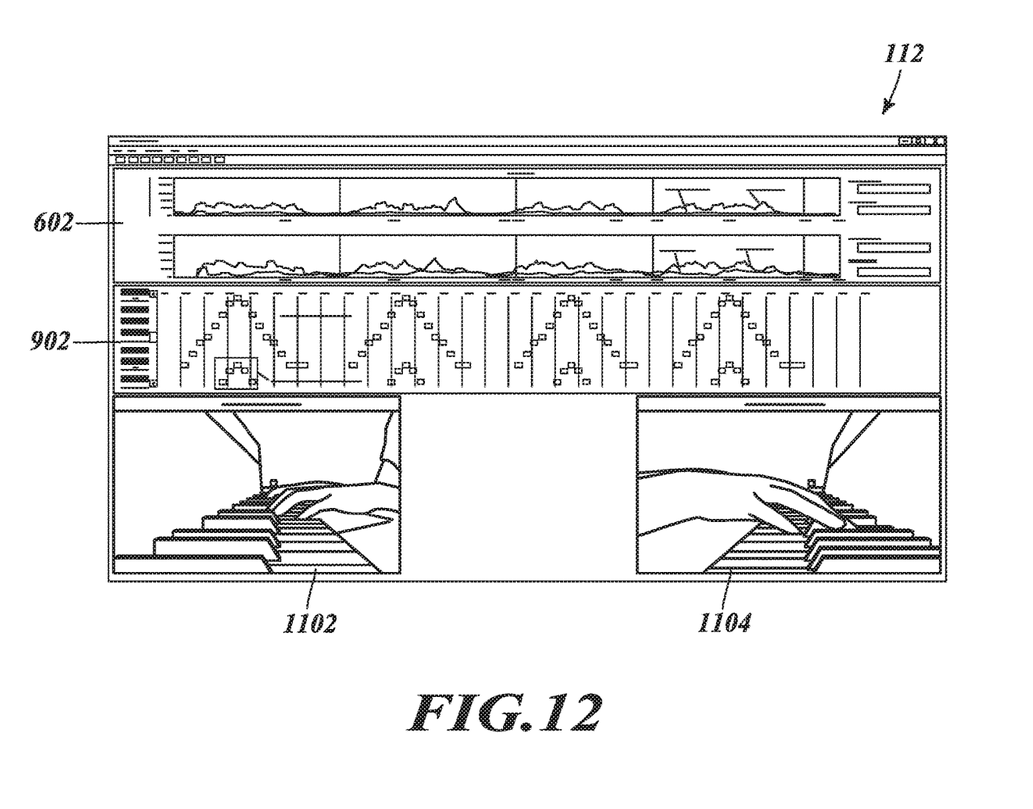
FIG. 12 is a schematic view of one embodiment of results of a biometric test being displayed concurrently on a display suitable for use with the biometric feedback system of FIG. 1, the results including the force data of FIG. 6, the muscle tension data of FIG. 9, and the video frames of FIG. 11, according to the invention.

FIG. 12 is a schematic view of one embodiment of results of a biometric test being displayed concurrently on the visual display 112. The results include the force data 602, the muscle tension data 902, and the video frames 1102a and 1102b. In at least some embodiments, each of the force data 602, the muscle tension data 902, and the video frames 1102a and 1102b are synchronized with one another, such that the data for each is shown concurrently. In at least some embodiments, the data for each is in real time. In at least some embodiments, the force data 602 and the muscle tension data 902 are positioned relative to one another such that the data sets are aligned (e.g., vertically, horizontally, or the like) with one another.

The one or more clinicians 206, the subject 202, or both, can observe the concurrently-displayed data and make adjustments, as needed, while the subject 202 performs the biometric test. Provided feedback from the one or more clinicians 206 may be gleaned from a combination of the displayed data. For example, in the embodiment shown in FIG. 2 of the subject 202 playing the keyboard 204, the force data may show a time point where the subject 202 is undesirably striking two keys at the same time. The muscle tension data at the same time point may show that the muscle tension in the subject's 202 forearms is undesirably high. This data could be interpreted as meaning that the undesirably-high muscle tension of the subject may be preventing the subject 202 from playing properly, as the muscle tension may be self-defeating (e.g., the muscle tension may be preventing the subject's 202 hands from efficiently utilizing muscles). The video from the same time point may show the subject 202 using incorrect hand posture (e.g., the subject's wrists may be drooping, or the like). The incorrect hand posture may, therefore, be determined to be the cause of the high muscle tension which, in turn, caused the subject 202 to undesirably strike two keys at the same time.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent is:

1. A biometric feedback system for providing biometric feedback to a subject while the subject performs a controlled physical movement to play music, the biometric feedback system comprising:
    an applied-force-recording interface and one or more controllers electrically coupled to the applied-force-recording interface, wherein the one or more controllers are configured and arranged to receive applied force from the subject while the subject performs the controlled physical movement to play the music, and wherein the applied-force-recording interface is configured and arranged to record one or more of an amount of force or a duration of force applied to the one or more controllers by the subject while the subject performs the controlled physical movement to play the music;
    a dynamic surface electromyograph ("sEMG") module and one or more sets of measuring electrodes electrically coupled to the dynamic sEMG module, wherein the one or more sets of measuring electrodes is configured and arranged for coupling to an exterior portion of the subject in proximity to one or more muscle groups and detecting action potentials along the one or more muscle groups, and wherein the dynamic sEMG module is configured and arranged to measure the detected action potentials while the subject performs the controlled physical movement to play the music, and wherein the one or more muscle groups include the left and right trapezius muscles and the left and right forearm extensor muscles;
    one or more video-recording devices are configured and arranged to capture one or more of a video or a static image of the subject performing the controlled physical movement to play the music; and
    a visual display configured and arranged to receive and display data provided by the applied-force-recording interface, the dynamic sEMG module and the one or more video-recording devices.

2. The biometric feedback system of claim 1, wherein the received data is displayed concurrently in real time.

3. The biometric feedback system of claim 1, wherein the system is configured such that the data collected from the applied-force-recording interface, the data collected from the dynamic sEMG module and the data collected from the one or more video-recording devices are viewable by a third person at a remote location.

4. The biometric feedback system of claim 1, further comprising one or more processors configured and arranged for providing processing power for processing the received data into one or more displayable images.

5. The biometric feedback system of claim 1, wherein the one or more video-recording devices includes a webcam.

6. The biometric feedback system of claim 1, wherein the one or more controllers is a musical instrument.

7. The biometric feedback system of claim 1, wherein the one or more controllers is an instrument with a tactile interface.

8. The biometric feedback system of claim 1, wherein the applied-force-recording interface is a musical instrument digital interface.

9. A method for providing biometric feedback to a subject as the subject performs a controlled physical movement using one or more controllers to play music, the method comprising:
    providing an applied-force-recording interface, one or more controllers electrically coupled to the applied-force-recording interface, wherein the one or more controllers are configured and arranged to receive applied force from the subject while the subject performs the controlled physical movement to play the music, and wherein the applied-force-recording interface is configured and arranged to record one or more of an amount of force or a duration of force applied to the one or more controllers by the subject while the subject performs the controlled physical movement to play the music;

providing an dynamic surface electromyograph ("sEMG") module and one or more sets of measuring electrodes electrically coupled to the dynamic sEMG module, wherein the one or more sets of measuring electrodes are configured and arranged for coupling to an exterior portion of the subject in proximity to one or more muscle groups and detecting action potentials along the one or more muscle groups, and wherein the dynamic sEMG module is configured and arranged to measure the detected action potentials while the subject performs the controlled physical movement to play the music, wherein the one or more muscle groups include the left and right trapezius muscles and the left and right forearm extensor muscles;

providing one or more video-recording devices configured and arranged to capture one or more of a video or a static image of the subject performing the controlled physical movement to play the music; and providing a visual display configured and arranged for receiving and displaying data provided by the applied-force-recording interface, the dynamic sEMG module and the one or more video-recording devices.

10. The method of claim 9, wherein the received data is displayed concurrently in real time.

11. The method of claim 9, wherein data collected from the applied-force-recording interface, the data collected from the dynamic sEMG module and the data collected from the one or more video-recording devices is viewable by a third person at a remote location.

12. The method of claim 9, further comprising one or more processors configured and arranged for providing processing power for processing the received data into one or more displayable images.

13. The method of claim 9, wherein the one or more video-recording devices includes a webcam.

14. The method of claim 9, wherein the one or more controllers includes a musical instrument.

15. The method of claim 9, wherein the one or more controllers includes an instrument with a tactile interface.

16. The method of claim 9, wherein the applied-force-recording interface is a musical instrument digital interface.

17. A computer-readable non-transitory media having processor-executable instructions for reading data from an applied-force-recording interface, a dynamic surface electromyography ("sEMG") device, and one or more video-recording devices as a subject performs a controlled physical movement to play music using one or more controllers coupled to the applied-force-recording interface, wherein the processor-executable instructions when installed onto a device enable the device to perform actions, comprising:

processing force data received from the applied-force-recording interface as the subject applies force to the one or more controllers to play music, the force data comprising one or more of an amount of force or a duration of force applied to the controller by the subject as the subject performs the controlled physical movement;

processing muscle tension data received from the dynamic sEMG device as the subject applies force to the one or more controllers to play music, the dynamic sEMG device comprising measuring electrodes and a dynamic sEMG module (106), wherein the muscle tension data comprising action potentials detected along two or more muscle groups by the measuring electrodes and measured by the dynamic sEMG module (106), and wherein the two or more muscle groups include the left and right trapezius muscles and the left and right forearm extensor muscles;

processing video data received from the at least one video-recording device, wherein the video data comprising one or more of a video or a static image of the subject captured as the subject performs the controlled physical movement to play the music; and displaying the processed data on a visual display, wherein the data collected from the applied-force-recording interface, the data collected from the dynamic sEMG module, and the data collected from the one or more video-recording devices is concurrently displayed.

18. The computer readable non-transitory media of claim 17, wherein the one or more controllers includes a musical instrument.

19. The computer readable non-transitory media of claim 17, wherein the one or more controllers includes an instrument with a tactile interface.

20. The computer readable non-transitory media of claim 17, wherein data collected from the applied-force-recording interface, the data collected from the dynamic sEMG module and the data collected from the one or more video-recording devices is viewable by a third person at a remote location.

* * * * *